United States Patent
Partridge et al.

(10) Patent No.: US 7,035,680 B2
(45) Date of Patent: Apr. 25, 2006

(54) CATHETER LEAD PLACEMENT SYSTEM AND METHOD

(75) Inventors: Scott Partridge, Blaine, MN (US); Christopher P. Knapp, Ham Lake, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 243 days.

(21) Appl. No.: 10/668,675

(22) Filed: Sep. 23, 2003

(65) Prior Publication Data

US 2005/0065419 A1 Mar. 24, 2005

(51) Int. Cl.
*A61B 5/04* (2006.01)
*A61N 1/05* (2006.01)

(52) U.S. Cl. .................. 600/374; 607/122; 607/126; 607/127; 607/128

(58) Field of Classification Search .............. 600/374; 607/122, 126–128
See application file for complete search history.

(56) References Cited

U.S. PATENT DOCUMENTS

| | | | | |
|---|---|---|---|---|
| 5,571,161 A | * | 11/1996 | Starksen | 607/122 |
| 6,836,687 B1 | * | 12/2004 | Kelley et al. | 607/122 |
| 2004/0215139 A1 | * | 10/2004 | Cohen | 604/95.04 |

* cited by examiner

*Primary Examiner*—Lee S. Cohen
(74) *Attorney, Agent, or Firm*—Hollingsworth & Funk, LLC

(57) ABSTRACT

A catheter system includes a mapping catheter having an open lumen and a mapping arrangement provided at a distal end of the mapping catheter. A balloon catheter is movably disposed within the open lumen of the mapping catheter. The balloon catheter has an open lumen dimensioned to receive a lead. A balloon arrangement is provided at a distal end of the balloon catheter and inflatable with an inflation mechanism provided at a proximal end of the balloon catheter. The balloon arrangement is dimensioned to prevent movement of the lead upon inflation of the balloon arrangement, and to permit movement of the lead within the open lumen of the balloon catheter upon deflation of the balloon arrangement.

56 Claims, 7 Drawing Sheets ically, one or more interior and/or exterior surfaces of the heart. For example, leads extending into the patient's heart are connected to electrodes that contact the myocardium for monitoring the heart's electrical signals and for delivering pulses to the heart in accordance with various therapies for treating arrhythmias.

CATHETER LEAD PLACEMENT SYSTEM AND METHOD

FIELD OF THE INVENTION

The present invention relates generally to leads for implantable cardiac stimulation devices, and, more particularly, to an endocardial electrode delivery system and method.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for monitoring the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of pacing and/or delivering high-energy shocks to the heart, interrupting ventricular tachyarrythmias or ventricular fibrillation, and allowing the heart to resume normal sinus rhythm.

An electrode of a typical endocardial lead is often implanted at an apical location within the heart. While apical placement is performed readily, it is often desirable to place leads at other locations, such as at the septum or along an outflow tract. Current systems and methods may not provide sufficient precision and capability for septal electrode placement desirable for optimum performance and improved patient outcomes.

SUMMARY OF THE INVENTION

A system in accordance with one embodiment of the present invention includes a mapping catheter having an open lumen and a mapping arrangement provided at a distal end of the mapping catheter. The catheter lumen is dimensioned to receive a medical electrical lead. A grasping arrangement is provided at a distal end of the catheter. A mechanism is provided at a proximal end of the balloon catheter to facilitate grasping and release of the medical electrical lead. The grasping arrangement is dimensioned to prevent movement of the lead upon grasping by the mechanism, and to permit movement of the lead within the open lumen of the balloon catheter upon release of the mechanism. The grasping arrangement may include one or more balloons that are annular, fluted, or otherwise configured to inflatably hold the lead in place. The grasping arrangement may be fluidly coupled to the proximal end of the mapping catheter to facilitate inflation and deflation of the balloon(s).

In accordance with another aspect of the present invention, a method of delivering a medical electrical lead includes advancing a mapping catheter into a cardiac structure via an access vessel. The cardiac structure is mapped using the mapping catheter to locate an appropriate implant site. A lead is inflatably held within the mapping catheter such that an electrode of the lead extends beyond a distal tip of the mapping catheter. Manipulating a proximal end of the lead implants the electrode into cardiac tissue at the implant site, and then the mapping catheter is removed.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
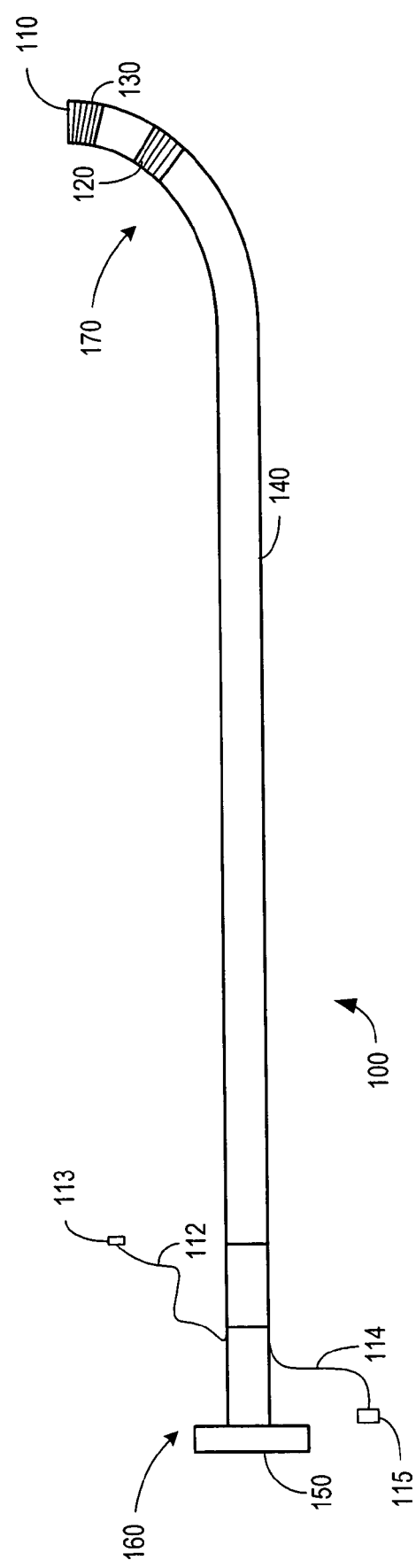
FIGS. 1A, 1B, and 1C are views of components of an endocardial lead placement system in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

Methods and devices employing endocardial leads in accordance with the present invention may incorporate one or more of the features, structures, methods, or combinations thereof described herein below. For example, an endocardial lead implantation system may be implemented to include one or more of the features and/or processes described below. It is intended that such a device or method need not include all of the features and functions described herein, but may be implemented to include one or more features and functions that, alone or in combination, provide for unique structures and/or functionality.

Systems, devices, and methods in accordance with the present invention can be implemented to facilitate implantation of leads for medical applications such as, for example, septal or outflow tract pacing for cardiac applications. For example, systems, devices, and methods in accordance with the present invention can facilitate implantation of a lead in the right chambers of the heart using catheters enabled for mapping and fixation purposes. Leads may be implanted without the use of stylets, enabling the use of leads having relatively smaller outside diameters.

Figure 1B:
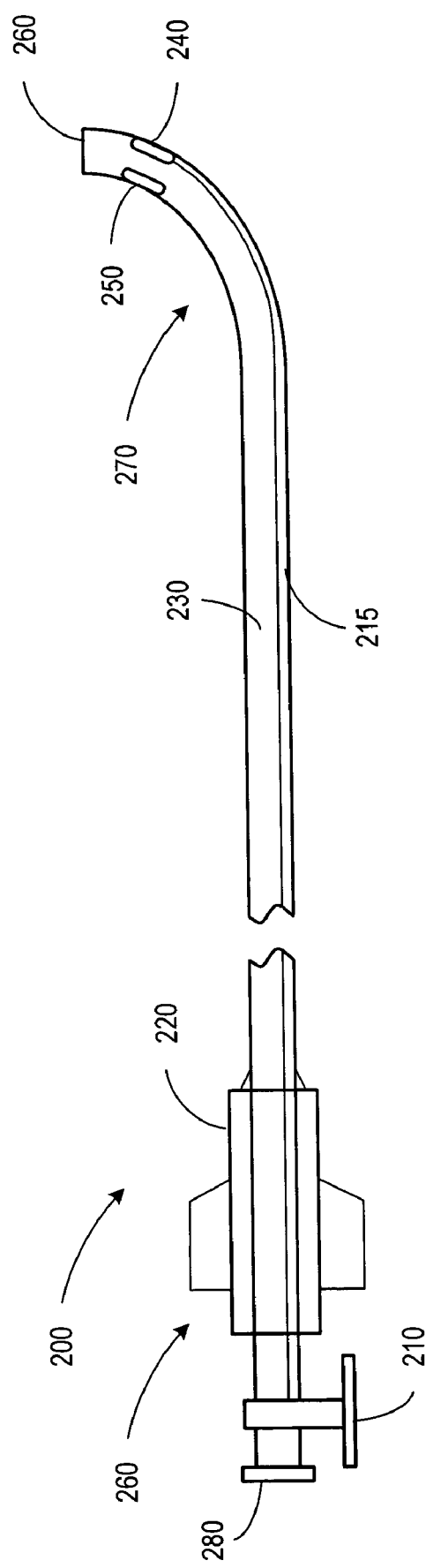
Figure 1C:
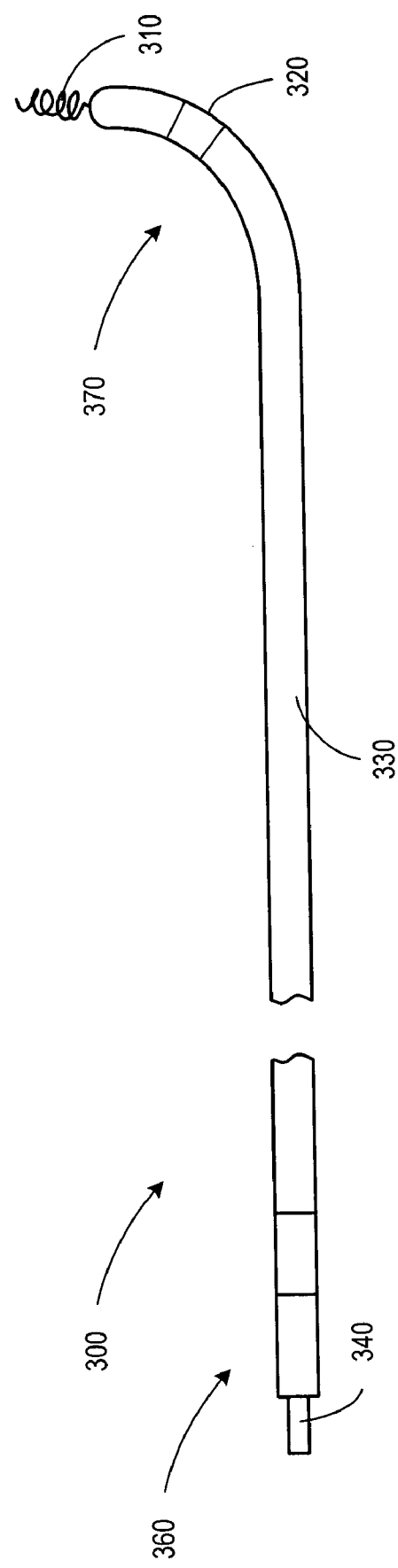

Referring to FIGS. 1A, 1B, and 1C, a lead placement system in accordance with the present invention is illustrated. The lead placement system includes a mapping catheter 100 (FIG. 1A), a balloon catheter 200 (FIG. 1B), and an endocardial lead 300 (FIG. 1C). The lead 300 is configured to fit within a lumen 260 of the balloon catheter 200. The balloon catheter 200 is configured to fit within a lumen 110 of the mapping catheter 100.

Referring to FIG. 1A, the mapping catheter 100 includes a body 140 having a proximal portion 160 and a distal portion 170. The distal portion 170 may include one or more mapping transducers and/or electrodes such as, for example, a first electrode 120 and a second electrode 130 that may act as a bipolar pair, or as individual electrodes. It is contemplated that other mapping transducers such as, for example, pressure transducers, accelerometers, microphones, or other sensing devices may be used in combination with, or in lieu of, the electrodes 120 and 130. The electrode 120 is connected to a first wire 112 terminating in a first connector 113. The electrode 130 is connected to a second wire 114 terminating in a second connector 115. An opening 150 provides access to the lumen 110 of the mapping catheter 100. Connectors 113 and 115 may be used to couple the mapping catheter 100 to amplifiers (not shown) for signal reception and/or transmission.

The aperture 150 of the mapping catheter 100 is configured to accept the balloon catheter 200 (FIG. 1B), and provide entry into the lumen 110 of the mapping catheter 100. Referring to FIG. 1B, the balloon catheter 200 includes a body 230 having a proximal portion 260 and a distal portion 270. The body 230 is configured to fit within the lumen 110 of the mapping catheter 100. The distal portion 270 includes a lumen 260, configured to include one or more grasping elements, such as a balloon 240 and a balloon 250. It is contemplated that other forms of grasping elements may be used to retain the lead 300 within the catheter 200 such as, for example, springs, a chuck, mechanical levers, or other suitable grasping means.

The balloon 240 is illustrated being connected to a fluid coupling 210 via an inflation lumen 215. The inflation lumen 215 provides for inflation and deflation of the balloons 240 and 250 by use of fluids such as, for example, air, water, or saline solution, injected or removed through the fluid coupling 210. The balloons 240 and 250 may be smooth, fluted, and/or have texturing or other means of altering the grasping quality and/or shape of the balloons 240 and 250. The balloons 240 and 250 may be implemented as sections of a single annular balloon, or may be representative of any number of balloons fluidly coupled to inflation lumen 215 or a number of inflation lumens.

The balloon catheter 200 is configured to be rotatable within the lumen 110 of the mapping catheter 100 by turning a rotation knob 220 (e.g., luer), illustrated at the proximal portion 260. A port 280 is provided at the proximal end of the balloon catheter 200 to allow insertion of the lead 300 (FIG. 1C) into the lumen 260.

Referring to FIG. 1C, the lead 300 includes a body 330 having a proximal portion 360 and a distal portion 370. The distal portion 370 is illustrated having a helical coil electrode 310 and a second electrode 320. It is contemplated that the lead 300 may include a fixation element, such as helical coil 310, where the coil is not used as an electrode. It is also contemplated that any type or number of electrodes may be used in accordance with the present invention (e.g., electrode 310 may be a non-helical tip electrode equipped with tines, barbs, springs, or the like.) For example, the electrode 310 may a unipolar electrode and/or form a bipolar pair with the electrode 320 for sensing and/or pacing in a first mode of operation. The electrode 320, which may be a coil electrode, may be used as a defibrillation electrode together with one or more other defibrillation electrodes (e.g., can electrode, or other coil electrode) in a second mode of operation. A connector 340 is provided at the proximal portion 360 to connect the lead 300 to a cardiac monitoring and/or stimulation device. The lead 300 may be solid, or may include an inner lumen providing access, for example, for a guide wire or a finishing wire as is known in the art.

Figure 2A:
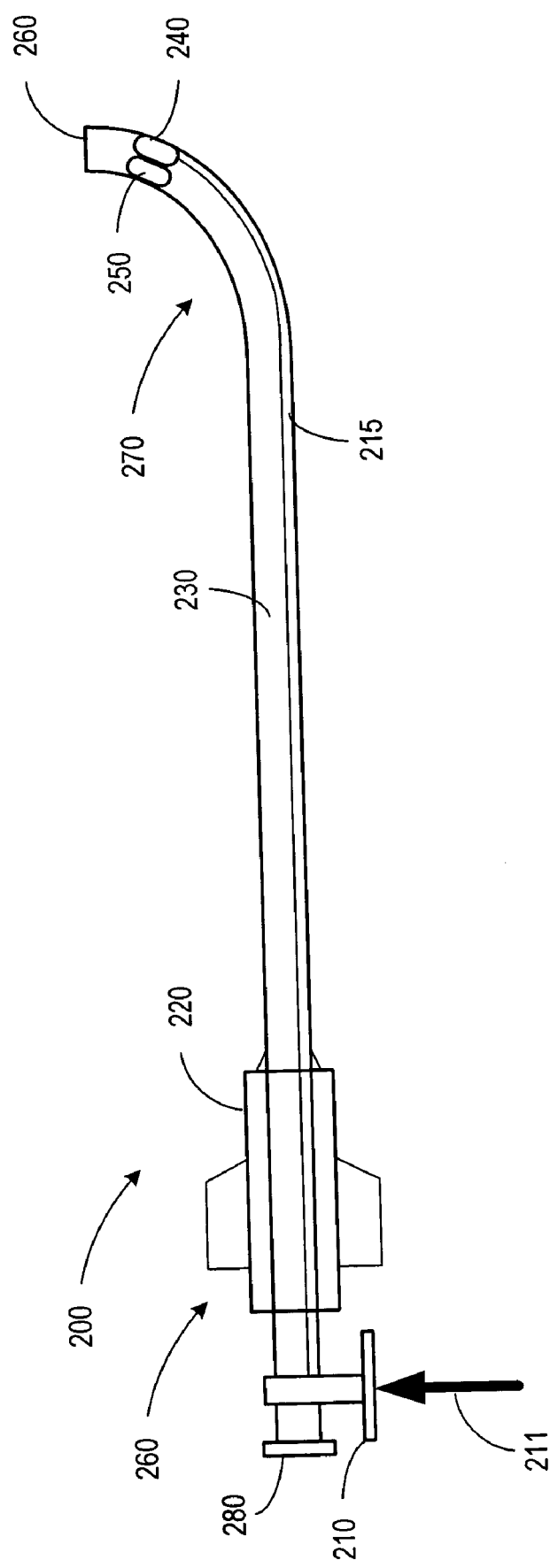
FIGS. 2A and 2B are plan views of a balloon catheter in accordance with an embodiment of the present invention with the balloon in an inflated (2A) and deflated (2B) configuration, respectively.
Figure 2B:
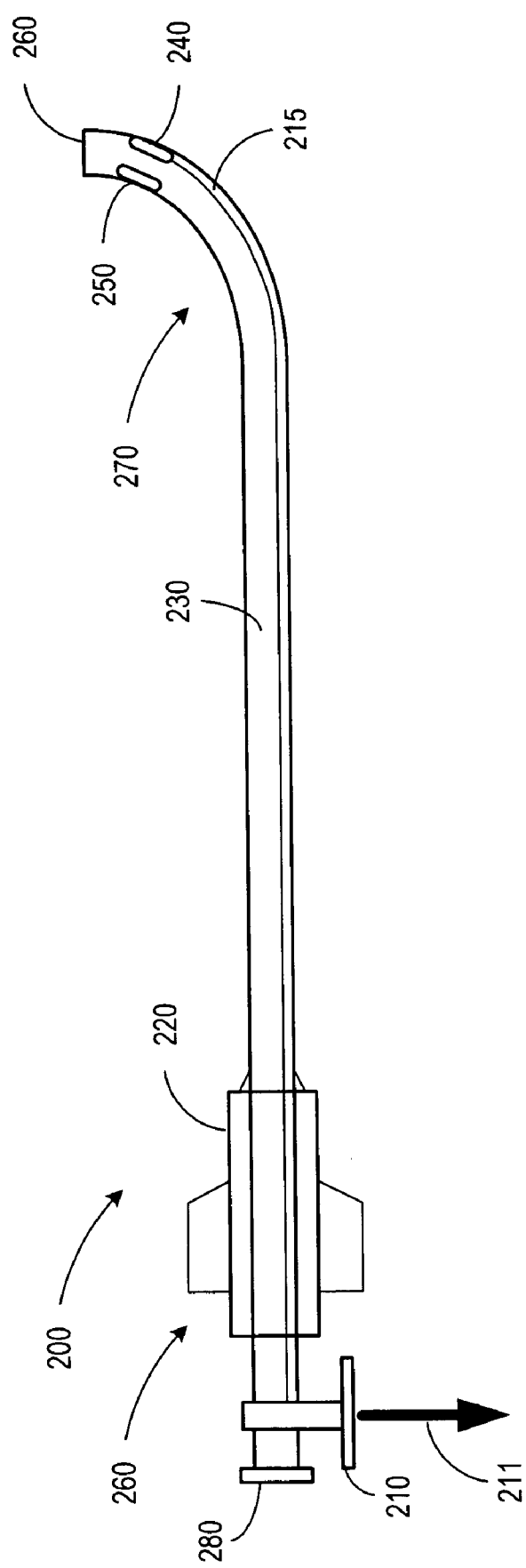

Referring to FIGS. 2A and 2B, the balloon catheter 200 is illustrated in an inflated and deflated configuration respectively. In FIG. 2A, the balloons 240 and 250 are shown in an inflated state. Balloons 240 and 250 constrict the lumen 260 at the distal portion 270. A saline injection 211 provides fluid pressure transmitted along the inflation lumen 215 and inflates the balloons 240 and 250 from their original state shown in FIG. 2B to their inflated states shown in FIG. 2A.

In FIG. 2B, the saline injection 211 is removed from the balloon catheter 200, allowing the balloons 240 and 250 to return to their deflated configuration. The fluid coupling 210 may be, for example, a stop-cock, allowing the balloons 240 and 250 to be held in their inflated states for a period of time sufficient to allow placement and fixation of the lead 300, as will be further described below.

Figure 3A:
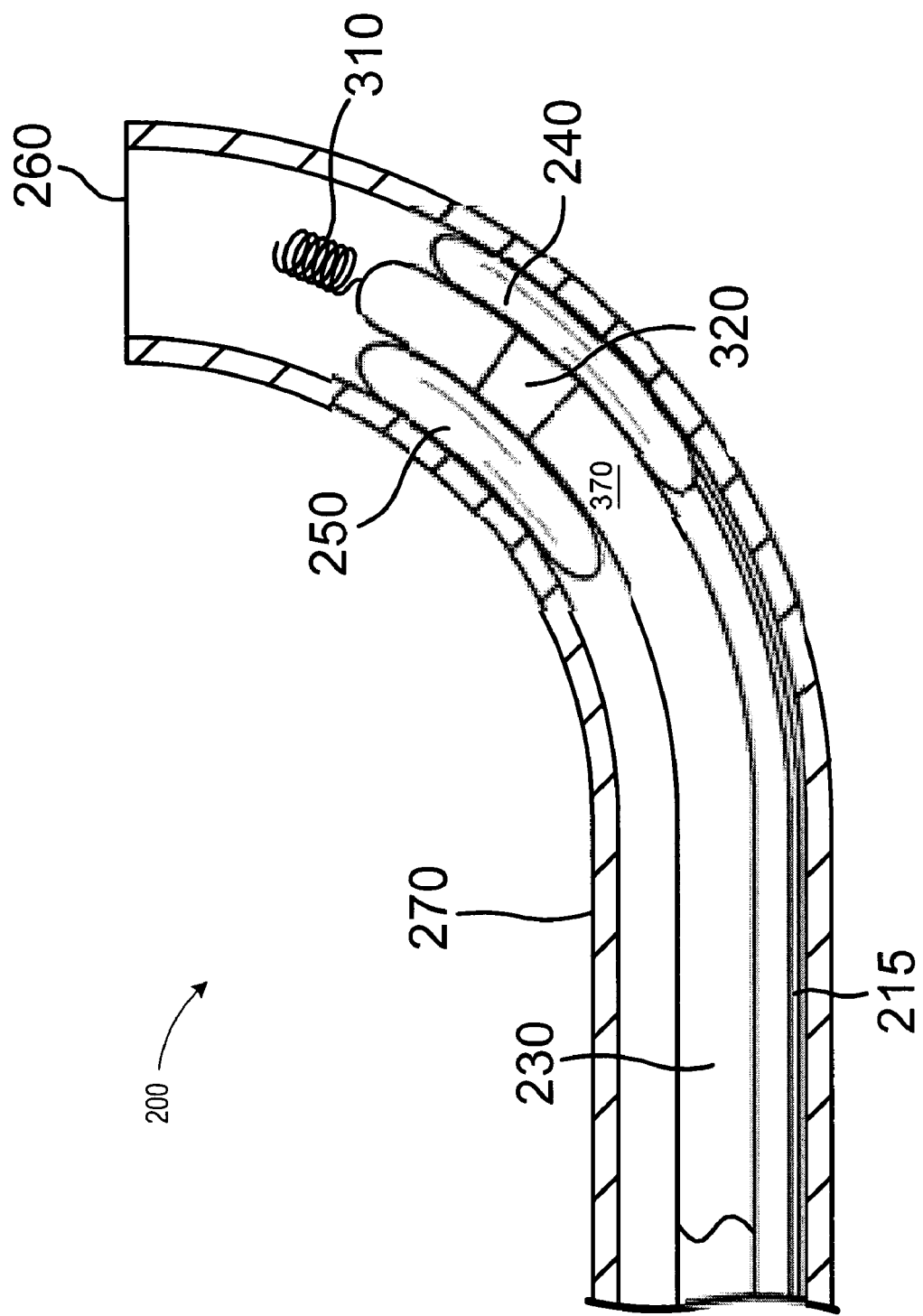
FIG. 3A is a magnified section drawing of an endocardial lead in a retracted position within a balloon catheter having an inflated balloon in accordance with an embodiment of the present invention.
Figure 3B:
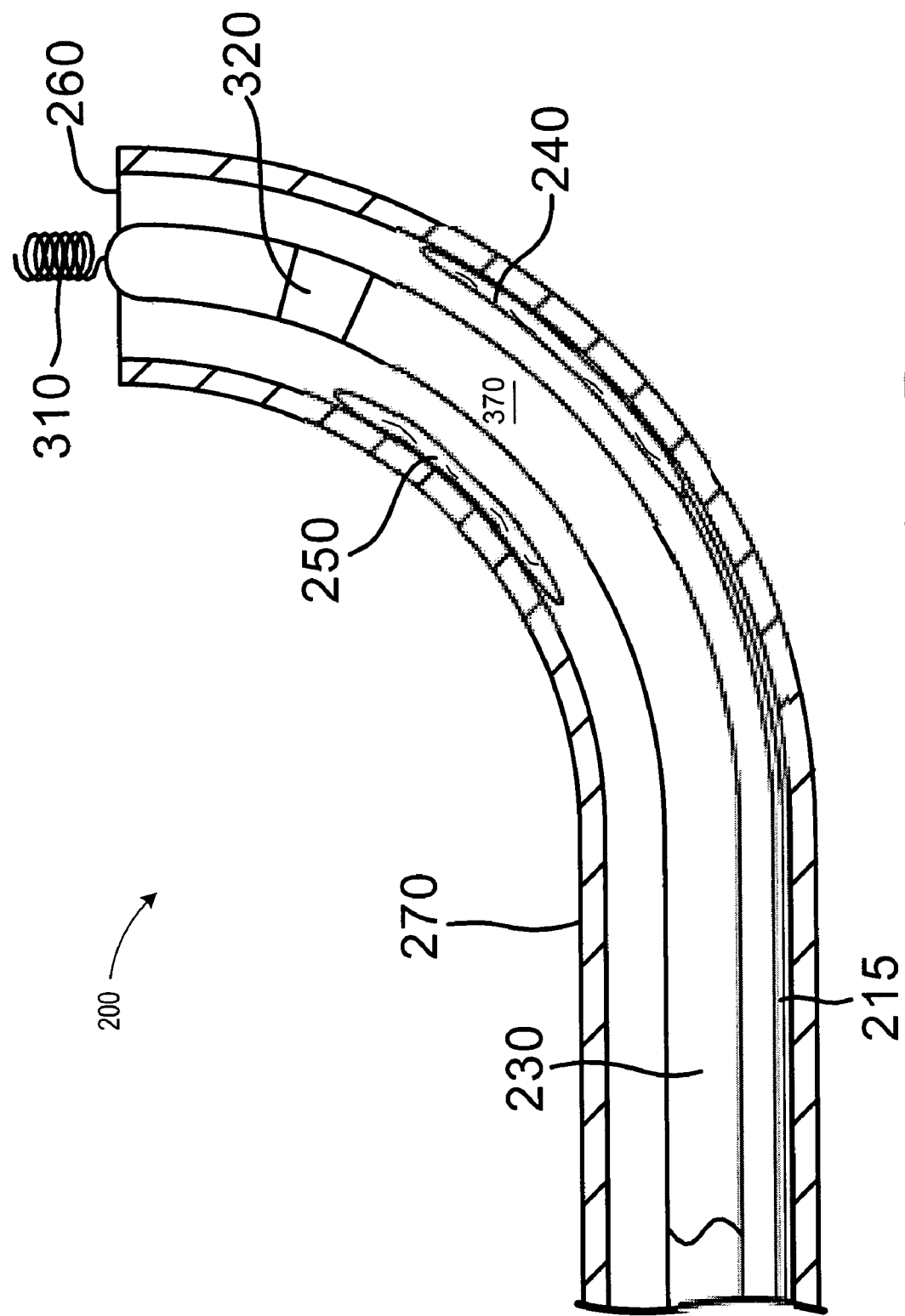
FIG. 3B is a magnified section drawing of an endocardial lead in an extended position within a balloon catheter having a deflated balloon in accordance with an embodiment of the present invention.

Referring to FIGS. 3A and 3B, the distal portion 370 of the lead 300 is shown grasped by the inflated balloons 240 and 250. The balloon catheter 200 may be advanced and positioned as desired within the mapping catheter 100 and positioned at a desired area of the anatomy for implantation. The balloons 240 and 250 are then deflated and the lead 300 is advanced (see FIG. 3B) until a desired length of the electrode 310 is exposed. The balloons 240 and 250 are re-inflated, and the balloon catheter 200 (FIG. 2B) is rotated by use of rotation knob 220 until the lead 300 is fixed at the implant site. It is contemplated that the lead 300 may be both advanced longitudinally and rotated within the balloon catheter 200 when in a deflated state for purposes of lead positioning and electrode fixation.

The balloon catheter 200 and the mapping catheter 100 may then be removed, leaving the lead 300 implanted at the desired location for use with a cardiac monitor and/or stimulation device. It is also contemplated that structures and/or functions of the balloon catheter 200 may be included within the mapping catheter 100, thereby eliminating extra componentry and allowing for an overall size reduction of the lead placement system.

Referring now to FIGS. 1A through 3B, methods in accordance with the present invention will be described. A method of delivering a medical electrical lead in accordance with the present invention involves advancing a mapping catheter 100 into a cardiac structure via an access vessel. The cardiac structure is mapped, using the mapping catheter 100, to locate an appropriate implant site. A lead 300 is insertable within the mapping catheter 100 such that the electrode 310 of the lead 300 is extendable and retractable beyond a distal tip of the mapping catheter 100. By manipulating a proximal end of the lead 300, the electrode 310 may be implanted into cardiac tissue at the implant site. The mapping catheter 100 is removed from the lead 300, leaving the lead implanted at the desired location.

The method may further include inflatably holding the lead 300 within the balloon catheter 200 such that the electrode 310 of the lead 300 extends beyond the distal tip of the balloon catheter 200. The balloon catheter 200 may be advanced through the mapping catheter 100 so that the electrode 310 contacts the implant site. Manipulating a proximal end of the balloon catheter 200 and/or lead 300 implants the electrode 310 into cardiac tissue at the implant site.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A catheter system, comprising:
   a mapping catheter comprising an open lumen and a mapping arrangement provided at a distal end of the mapping catheter; and
   a balloon catheter movably disposed within the open lumen of the mapping catheter, the balloon catheter comprising:
      an open lumen dimensioned to receive a medical electrical lead;
      a balloon arrangement provided at a distal end of the balloon catheter and inflatable within the open lumen of the balloon catheter; and
      an inflation mechanism provided at a proximal end of the balloon catheter and fluidly coupled to the balloon arrangement facilitating inflation and deflation of the balloon arrangement, the balloon arrangement dimensioned to prevent movement of the lead upon inflation of the balloon arrangement, and to permit movement of the lead within the open lumen of the balloon catheter upon deflation of the balloon arrangement.

2. The system of claim 1, wherein the balloon arrangement comprises at least one annular balloon.

3. The system of claim 1, wherein the balloon arrangement comprises at least one fluted balloon.

4. The system of claim 1, wherein the balloon catheter comprises an inflation lumen provided along a length of the balloon catheter, and the balloon arrangement comprises a unitary balloon fluidly coupled to the inflation mechanism via the inflation lumen.

5. The system of claim 1, wherein the balloon catheter comprises a plurality of inflation lumens respectively provided along a length of the balloon catheter, and the balloon arrangement comprises a plurality of balloons each fluidly coupled to the inflation mechanism via the inflation lumens.

6. The system of claim 1, wherein the balloon catheter is longitudinally displaceable and rotatable within the open lumen of the mapping catheter.

7. The system of claim 1, wherein the mapping arrangement comprises bipolar mapping electrodes.

8. The system of claim 1, wherein the mapping arrangement comprises one or more accelerometers.

9. The system of claim 1, wherein the mapping arrangement comprises one or more acoustic sensors.

10. The system of claim 1, wherein the lead comprises a fixation arrangement disposed at a distal tip of the lead, and the balloon arrangement engages the lead upon inflation of the balloon arrangement with a force that permits implanting of the fixation arrangement into cardiac tissue.

11. The system of claim 1, wherein the lead comprises a helical fixation element disposed at a distal tip of the lead, and the balloon arrangement engages the lead upon inflation of the balloon arrangement with a force that permits rotational implanting of the helical fixation element into cardiac tissue.

12. A lead delivery system, comprising:
    a medical electrical lead;
    a mapping catheter comprising an open lumen and a mapping arrangement provided at a distal end of the mapping catheter; and
    a balloon catheter movably disposed within the open lumen of the mapping catheter, the balloon catheter comprising:
       an open lumen dimensioned to receive the lead;
       a balloon arrangement provided at a distal end of the balloon catheter and inflatable within the open lumen of the balloon catheter; and
       an inflation mechanisms provided at a proximal end of the balloon catheter and fluidly coupled to the balloon arrangement facilitating inflation and deflation of the balloon arrangement, the balloon arrangement dimensioned to grasp the lead upon inflation of the balloon arrangement, and to permit movement of the lead within the open lumen of the balloon catheter upon deflation of the balloon arrangement.

13. The system of claim 12, wherein the medical electrical lead comprises a pacing lead.

14. The system of claim 12, wherein the medical electrical lead comprises a defibrillation lead.

15. The system of claim 12, wherein the medical electrical lead comprises a pacing lead comprising an open lumen.

16. The system of claim 15, wherein the open lumen of the pacing lead is dimensioned to receive a guide wire or a finishing wire.

17. The system of claim 12, wherein the medical electrical lead comprises a lead having a closed lumen.

18. The system of claim 12, wherein the medical electrical lead comprises an active fixation mechanism.

19. The system of claim 12, wherein the medical electrical lead comprises a helical electrode.

20. The system of claim 12, wherein the medical electrical lead comprises fixation tines.

21. The system of claim 12, wherein the medical electrical lead comprises an extendable/retractable fixation element.

22. The system of claim 12, wherein the medical electrical lead comprises one or more spring-biased fixation elements.

23. The system of claim 12, wherein the medical electrical lead comprises a tip electrode configured for unipolar operation.

24. The system of claim 12, wherein the medical electrical lead comprises a tip electrode and a ring electrode configured for bipolar operation.

25. The system of claim 12, wherein the balloon arrangement comprises at least one annular balloon.

26. The system of claim 12, wherein the balloon arrangement comprises at least one fluted balloon.

27. The system of claim 12, wherein the balloon catheter comprises an inflation lumen provided along a length of the balloon catheter, and the balloon arrangement comprises a unitary balloon fluidly coupled to the inflation mechanism via the inflation lumen.

28. The system of claim 12, wherein the balloon catheter comprises a plurality of inflation lumens respectively provided along a length of the balloon catheter, and the balloon arrangement comprises a plurality of balloons each fluidly coupled to the inflation mechanism via the inflation lumens.

29. The system of claim 12, wherein the mapping arrangement comprises one or more accelerometers.

30. The system of claim 12, wherein the mapping arrangement comprises one or more acoustic sensors.

31. The system of claim 12, wherein mapping arrangement comprises bipolar mapping electrodes.

32. The system of claim 12, wherein the balloon catheter is longitudinally displaceable and rotatable within the open lumen of the mapping catheter.

33. The system of claim 12, wherein the lead comprises a fixation arrangement disposed at a distal tip of the lead, and the balloon arrangement engages the lead upon inflation of the balloon arrangement with a force that permits implanting of the fixation arrangement into cardiac tissue.

34. The system of claim 12, wherein the lead comprises a helical fixation element disposed at a distal tip of the lead, and the balloon arrangement engages the lead upon inflation of the balloon arrangement with a force that permits rotational implanting of the helical fixation element into cardiac tissue.

35. A method of delivering a medical electrical lead, comprising:
    advancing a mapping catheter into a cardiac structure via an access vessel;
    mapping, using the mapping catheter, the cardiac structure to locate an appropriate implant site;
    inflatably holding the lead within a balloon catheter such that an electrode of the lead extends beyond a distal tip of the balloon catheter;
    advancing the balloon catheter though the mapping catheter so that the electrode contacts the implant site;
    manipulating a proximal end of the balloon catheter to implant the electrode into cardiac tissue at the implant site; and
    removing the balloon and mapping catheters.

36. The method of claim 35, wherein removing the balloon and mapping catheters comprises:
    depressurizing the balloon catheter to permit relative movement between the balloon catheter and the lead;
    retracting the balloon catheter in a proximal direction to remove the balloon catheter from the mapping catheter; and
    removing the mapping catheter from the cardiac structure and the access vessel.

37. The method of claim 35, wherein manipulating the proximal end of the balloon catheter comprises rotatably manipulating the proximal end of the balloon catheter.

38. The method of claim 35, wherein manipulating the proximal end of the balloon catheter comprises longitudinally manipulating the proximal end of the balloon catheter.

39. The method of claim 35, wherein manipulating the proximal end of the balloon catheter comprises increasing pressurization of the balloon catheter when implanting the electrode into the cardiac tissue.

40. The method of claim 35, wherein manipulating the proximal end of the balloon catheter comprises rotating the proximal end of the balloon catheter and increasing pressurization of the balloon catheter when rotatably implanting the electrode into the cardiac tissue.

41. The method of claim 35, wherein inflatably holding the lead further comprises inflating one or more inflation balloons disposed at a distal end of the balloon catheter such that the one or more inflation balloons forceably engage the lead.

42. The method of claim 35, wherein inflatably holding the lead further comprises advancing the lead through the balloon catheter until the electrode extends beyond the distal tip of the balloon catheter prior to advancing the balloon catheter through the mapping catheter.

43. The method of claim 35, wherein mapping the cardiac structure comprises mapping a plurality of cardiac structure locations until electrical parameters indicate that the appropriate implant site has been located.

44. The method of claim 35, further comprising verifying electrical performance of the implanted lead and repositioning the electrode in the cardiac structure if a nominal electrical performance level is not achieved.

45. A lead delivery system for facilitating implantation of a lead electrode into cardiac tissue, comprising:
    a mapping catheter comprising an open lumen, a proximal end, and a distal end provided with one or more mapping electrodes; and
    an inner catheter movably disposed within the open lumen of the mapping catheter, the inner catheter comprising an open lumen, a proximal end, a distal end, a grasping mechanism disposed within the open lumen at the distal end of the inner catheter, and an activation mechanism provided at the proximal end of the inner catheter, the open lumen of the inner catheter dimensioned to receive a lead and to restrict movement of the lead's distal end at the inner catheter's distal end in response to activation of the grasping mechanism.

46. The lead delivery system of claim 45, wherein the grasping mechanism comprises one or more balloons adapted to inflatably grasp the lead.

47. The lead delivery system of claim 45, wherein the inner catheter is longitudinally displaceable and rotatable within the open lumen of the mapping catheter.

48. The lead delivery system of claim 45, wherein the mapping catheter comprises bipolar mapping electrodes.

49. The lead delivery system of claim 45, wherein the mapping catheter comprises one or more accelerometers or one or more acoustic sensors.

50. A method of delivering a medical electrical lead, comprising:
    advancing a mapping catheter into a cardiac structure via an access vessel;
    mapping, using the mapping catheter, the cardiac structure to locate an appropriate implant site;
    inflatably holding a lead within the mapping catheter such that an electrode of the lead extends beyond a distal tip of the mapping catheter;
    manipulating a proximal end of the lead to implant the electrode into cardiac tissue at the implant site; and
    removing the mapping catheter.

51. The method of claim 50, wherein mapping the cardiac structure comprises mapping a plurality of cardiac structure locations until electrical parameters indicate that the appropriate implant site has been located.

52. The method of claim 50, further comprising rotatably implanting the electrode into the cardiac tissue.

53. The method of claim 50, further comprising fixing the electrode into the cardiac tissue using a helical fixation element.

54. The method of claim 50, further comprising fixing the electrode into the cardiac tissue using an extendable/retractable fixation element.

55. The method of claim 50, further comprising fixing the electrode into the cardiac tissue using one or more tines for fixation.

56. The method of claim 50, further comprising fixing the electrode into the cardiac tissue using a spring-biased fixation element.

* * * * *

UNITED STATES PATENT AND TRADEMARK OFFICE
CERTIFICATE OF CORRECTION

PATENT NO. : 7,035,680 B2
APPLICATION NO. : 10/668675
DATED : April 25, 2006
INVENTOR(S) : Partridge et al.

It is certified that error appears in the above-identified patent and that said Letters Patent is hereby corrected as shown below:

In the Specification

Col. 1, line 25: "Typical Implantable" should read --Typical implantable--.

Col. 1, line 29: "ventricular tachyarrythmias" should read --ventricular tachyarrhythmias--.

Col. 4, line 2: "may a unipolar" should read --may be unipolar--.

In the Claims

Claim 12, column 6 line 16: "inflation mechanisms provided" should read --inflation mechanism provided--.

Claim 31, column 7 line 3: "wherein mapping" should read --wherein the mapping--.

Claim 35, column 7 line 28: "catheter though the mapping" should read --catheter through the mapping--.

Signed and Sealed this

Twenty-third Day of January, 2007

JON W. DUDAS
*Director of the United States Patent and Trademark Office*